United States Patent
Yamamoto et al.

(10) Patent No.: US 7,374,901 B2
(45) Date of Patent: May 20, 2008

(54) METHOD OF ANALYZING COENZYME Q-10 AND TWO-ELECTRON REDUCTION PRODUCT THEREOF AND ANALYSIS SYSTEM

(75) Inventors: Yorihiro Yamamoto, Tokyo (JP); Masashi Mita, Tokyo (JP)

(73) Assignee: Shiseido Company Ltd., Tokyo (JP)

( * ) Notice: Subject to any disclaimer, the term of this patent is extended or adjusted under 35 U.S.C. 154(b) by 0 days.

(21) Appl. No.: 10/537,338

(22) PCT Filed: Dec. 3, 2003

(86) PCT No.: PCT/JP03/15478

§ 371 (c)(1), (2), (4) Date: Nov. 21, 2005

(87) PCT Pub. No.: WO2004/051259

PCT Pub. Date: Jun. 17, 2004

(65) Prior Publication Data

US 2006/0148025 A1    Jul. 6, 2006

(30) Foreign Application Priority Data

Dec. 3, 2002  (JP) .............. 2002-351677
Dec. 1, 2003  (JP) .............. 2003-401940

(51) Int. Cl.
C12Q 1/26   (2006.01)
C12P 7/66   (2006.01)
A61K 49/00  (2006.01)
A61K 38/00  (2006.01)

(52) U.S. Cl. .................. 435/25; 435/133; 424/9.1; 514/2; 514/690

(58) Field of Classification Search .......... None
See application file for complete search history.

(56) References Cited

U.S. PATENT DOCUMENTS

2002/0125193 A1   9/2002  Tang et al.

FOREIGN PATENT DOCUMENTS

| EP | 0 956 854 A1 | 11/1999 |
|----|----|----|
| JP | 55-039701 | 3/1980 |
| JP | 58-092609 | 6/1983 |
| JP | 61-293391 | 12/1986 |
| WO | WO 03/056024 | 7/2003 |

OTHER PUBLICATIONS

Edlund, PO (1988) Determination of Coenzyme Q10, alpha tocopherol and cholesterol in biological samples by coupled-column liquid chromatography with coulometreic and ultraviolet detection. J Chromatogr B 425: pp. 87-97.*

Grossi G et al (1992) Improved high-performance liquid chromatographic method for the determination of coenzyme Q10 in plasma. J Chromatogr 593: pp. 217-226.*

Mosca F et al (published online Apr. 25, 2002) Assay of coenzyme Q10 in plasma by a single dilution step. Anal Biochem, vol. 305, pp. 49-54.*

Yamashita, S., et al., "Simultaneous Detection of Ubiquinol and Ubiquinone in Human Plasma as a Marker of Oxidative Stress," *Analytical Biochemistry*, 250 (1997), pp. 66-73.

Edlund, P., "Determination of Coenzyme $Q_{10}$ α-Tocopherol and Cholesterol in Biological Samples by Coupled-Column Liquid Chromatography with Coulometric and Ultraviolet Detection," *Journal of Chromatography*, 425(1988) pp. 87-97.

* cited by examiner

*Primary Examiner*—Lisa J. Hobbs (57) ABSTRACT

The present invention relates to an analysis method and analysis system that can accurately analyze the contents of coenzyme Q-10 and a 2-electron reduced form thereof in a specimen, in which human blood plasma as the specimen is mixed with isopropyl alcohol as a pretreatment and the coenzyme Q-10 and the 2-electron reduced form thereof are extracted to the isopropyl alcohol. Extracted liquid is stored at a temperature of 4° C. until the analysis is performed. The extracted liquid as an analytical sample is analyzed by an analysis system provided with a liquid-sending mechanism, a switching mechanism, a concentration column, a separation column, a reduction column, an ultraviolet absorption detector, and an electrochemical detector.

4 Claims, 7 Drawing Sheets

METHOD OF ANALYZING COENZYME Q-10 AND TWO-ELECTRON REDUCTION PRODUCT THEREOF AND ANALYSIS SYSTEM

TECHNICAL FIELD

The present invention relates to an analysis method and analysis system for coenzyme Q-10 and a 2-electron reduced form thereof.

BACKGROUND ART

Coenzyme Q (Coenzyme Q: CoQ) is a benzoquinone derivative and is named as a ubiquinone since it widely exists in the living world. A hydroquinone obtained by 2-electron-reducing a ubiquinone is a ubiquinol.

The compound name of the ubiquinone is 2,3-dimethoxy-5-methyl-6-polyprenyl-1,4-benzoquinone, and a great number of homologs with n=1 through 12 isoprene units naturally exist, wherein n=10 for higher animals such as humans. In the following description, a ubiquinone of humans, etc., is represented as coenzyme Q-10 and a ubiquinol of humans, etc., is represented as a 2-electron reduced form of coenzyme Q-10, as long as no particular reference is made.

The 2-electron reduced form of coenzyme Q-10 has a strong oxidative effect and is considered to have an antiaging effect such as the prevention of cellular damage caused by active oxygen.

Oxidation stress is considered to be an undesired state for an organism in which the balance between oxidation and antioxidation in the organism is disrupted so as to shift toward oxidation, and it is considered that the ratio of the coenzyme Q-10 and the 2-electron reduced form thereof can be a good marker for oxidation stress since it is considered to reflect the degree of oxidation stress.

Thus, since it is very useful to know the behaviors of the coenzyme Q-10 and the 2-electron reduced form thereof, a method for accurately analyzing these components is desired.

As a conventional analysis method, an ultraviolet absorption method, etc., is provided but it is easily subjected to the influence of a third substance and, therefore, a complicated pretreatment is required.

In recent years, a high-performance liquid chromatography (referred to as a HPLC below) has been widely used as a method that can attain a highly sensitive and accurate analysis. For the detection of coenzyme Q-10, ultraviolet absorption at 275 nm is utilized. However, the sensitivity of the conventional analysis method by means of a HPLC is not enough to detect coenzyme Q-10 in blood plasma.

For this reason, a method of reducing coenzyme Q-10 to a 2-electron reduced form thereof for quantifying the difference between the quantities of the coenzyme Q-10 before and after the reduction is also suggested. However, in this analysis method, it is necessary to perform a pretreatment on a specimen and to twice perform sample injections into a HPLC.

Figure 1:
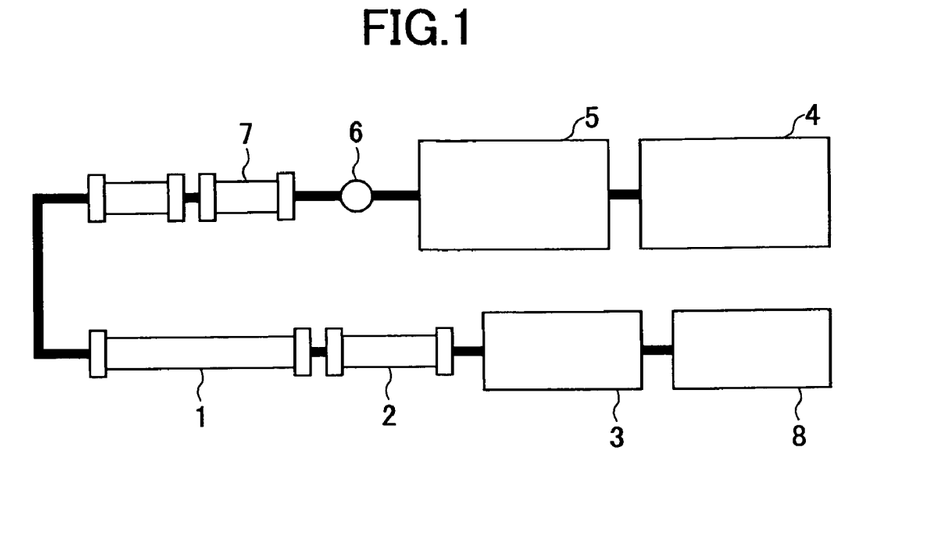
FIG. 1 is a diagram showing a general configuration of a conventional analysis system for coenzyme Q-10 and a 2-electron reduced form thereof.

Therefore, the applicants previously suggested a method such that after coenzyme Q-10 and a 2-electron reduced form thereof are separated by a reversed phase separation column 1 (LC-8 produced by SUPELCO), the coenzyme Q-10 is reduced to a 2-electron reduced form thereof using a reduction column 2 (SHISEIDO CQ produced by Shiseido Co., Ltd.) or coulometric electrodes, which reduced forms are measured by an electrochemical detector 3, as shown in FIG. 1 (For example, see Satosi Yamasita and Yorihiro Yamamoto, ANALYTICAL BIOCHEMISTRY, 250, 66-73 (1997)). Herein, in FIG. 1, reference numerals 4, 5, 6, 7, and 8 denote a mobile phase, a pump, a sample injector, a protection column, and an ultraviolet absorption detector, respectively.

Figure 2:
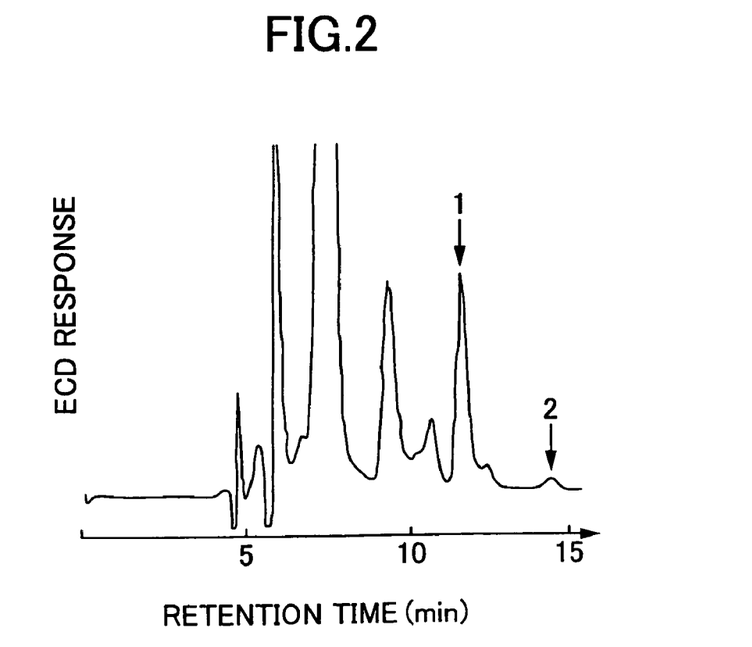
FIG. 2 is one example of a chromatogram obtained by an analysis system in FIG. 1.

The highly sensitive simultaneous measurement of the coenzyme Q-10 and the 2-electron reduced form thereof can be attained using the analysis method described above. One example of an obtained chromatogram is shown in FIG. 2. In FIG. 2, "1" denotes a peak for the coenzyme Q-10 and "2" denotes a peak for the 2-electron reduced form of the coenzyme Q-10.

In this case, since the measurement is influenced by a water-soluble antioxidation substance in the specimen, such as vitamin C and uric acid, etc., a pretreatment is performed for subjecting the specimen to an extraction treatment with methanol/hexane so as to distribute the water-soluble antioxidation substance into a methanol phase and the coenzyme Q-10, etc., into a hexane phase.

Figure 3A:
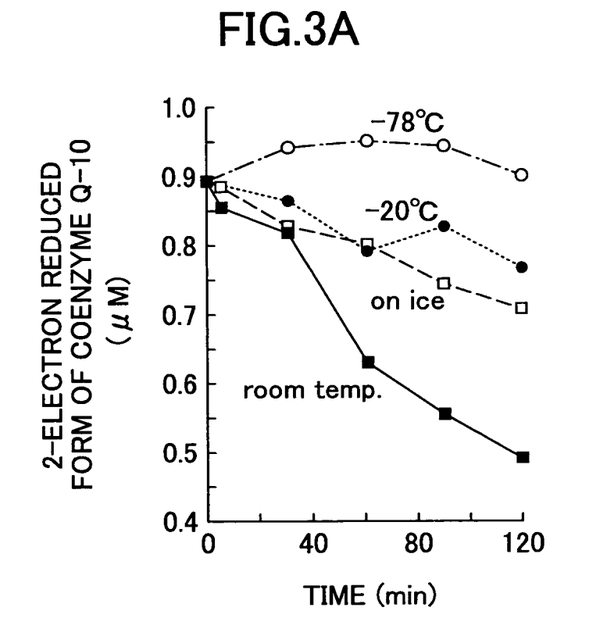
FIG. 3A is a graph diagram showing variation in a component with time when a specimen under test for the analysis system in FIG. 1 is stored, with respect to a 2-electron reduced form of coenzyme Q-10.
Figure 3B:
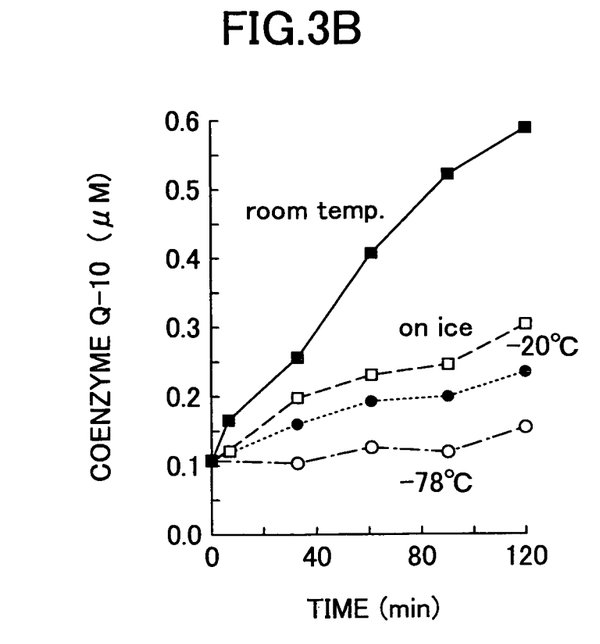
FIG. 3B is a graph diagram showing variation in a component with time when a specimen under test for the analysis system in FIG. 1 is stored, with respect to coenzyme Q-10.

However, when pretreatment is performed subjecting the specimen to the extraction treatment with methanol/hexane, the coenzyme Q-10 in the hexane extraction liquid is chemically unstable. After the pretreatment and until the pretreated liquid is injected into a HPLC for analysis, the 2-electron reduced form of coenzyme Q-10 is oxidized at a substantial rate as shown in FIG. 3. It is therefore necessary to perform analysis immediately after the extraction of the specimen. For performing an accurate analysis, since it is essential to perform an extraction process immediately before the injection into the HPLC, it is significantly difficult to treat a large amount of specimen collectively. Herein, each temperature indicates a storage temperature of the hexane extraction liquid in FIG. 3.

DISCLOSURE OF THE INVENTION

It is a general object of the present invention to provide an analysis method and analysis system for coenzyme Q-10 and a 2-electron reduced form thereof which can solve the problems of the conventional techniques as described above.

A more specific object of the present invention is to realize an analysis method and analysis system which can accurately quantify the contents of coenzyme Q-10 and a 2-electron reduced form thereof in a specimen.

For achieving the objects, as a result of keen examinations by the applicants, it has been found that the employment of isopropyl alcohol as an extraction solvent used for the pretreatment instead of methanol/hexane is preferable. The following invention is made based on this evidence.

An analysis method for coenzyme Q-10 and a 2-electron reduced form thereof according to the present invention is characterized in that a specimen containing at least one of coenzyme Q-10 and a 2-electron reduced form thereof is extracted with an water-soluble organic solvent as a pretreatment and the extracted liquid as an analytical sample is analyzed.

Herein, the coenzyme Q-10 indicates a ubiquinone and the 2-electron reduced form of coenzyme Q-10 indicates a ubiquinol, as described above. The water-soluble organic solvent is preferably isopropyl alcohol but is not limited to it, and a solvent having a polarity comparable to that of isopropyl alcohol can be employed. For example, a mixed solvent of which the polarity is adjusted by mixing methanol, ethanol, butanol, and n-propyl alcohol, etc., can be employed. Additionally, an analysis method for an analytical sample after the pretreatment is not limited to the analysis method according to the present invention as described below, and an appropriate method such as the above-mentioned conventional analysis method can be also employed.

Due to the above-mentioned configuration of the present invention, the variation in a component until the analysis of an analytical sample can be suppressed for an accurate analysis. Also, it is not necessary to perform the analysis immediately after extracting a specimen.

In this case, if the extracted liquid is stored at a temperature within a range of the melting point of the extracted liquid through room temperature, more preferably a temperature of around 4° C., until the extracted liquid is analyzed, then the variation in a component can be suppressed more certainly, which is preferable. Herein, the melting point of the extracted liquid is substantially equal to the melting point of the water-soluble organic solvent used for the extraction.

Also, in this case, if a preparatory treatment for condensing the analytical sample (extracted liquid) is performed according to a column switching method, then even if the concentrations of coenzyme Q-10 and a 2-electron reduced form thereof are low, an accurate and highly sensitive analysis can be performed, which is preferable.

Also, in this case, if an extracted liquid from a specimen containing both coenzyme Q-10 and a 2-electron reduced form thereof is the analytical sample and the coenzyme Q-10 and the 2-electron reduced form thereof are separated by a column, further subjected to a reduction treatment, and subsequently detected by a detector, then it is not necessary to twice inject the analytical sample into a HPLC as in the conventional technique and an efficient analysis can be performed, which is preferable.

Also, in order to preferably realize the analysis method according to the present invention, an analysis system for coenzyme Q-10 and a 2-electron reduced form thereof is an analysis system used for the analysis method for coenzyme Q-10 and a 2-electron reduced form thereof, characterized by having a liquid-sending mechanism that includes a first series for liquid-sending an analytical sample with a first mobile phase and a second series for liquid-sending only a second mobile phase, a switching mechanism for switching liquid-sending routes for the mobile phases of the two series of the liquid-sending mechanisms, a condensation column for receiving the second mobile phase after the mobile phase of the first series is received so as to condense the analytical sample, a separation column for receiving and separating liquid sent from the condensation column, a reduction column for receiving and reducing liquid sent from the separation column, and an electrochemical detector for detection-processing liquid sent from the reduction column.

In this case, if further having an ultraviolet absorption detector as a detector, a simultaneous analysis of a component in a specimen which component cannot be detected with high sensitivity by electrochemical detection, such as cholesterol, etc., can be performed, which is preferable.

BRIEF DESCRIPTION OF THE DRAWINGS

Other objects, features and advantages of the present invention will become more apparent when reading the following detailed description with reference to the accompanying drawings, in which.

BEST MODE FOR CARRYING OUT THE INVENTION

Next, a preferred embodiment (referred to as an example, below) of an analysis method and analysis system for coenzyme Q-10 and a 2-electron reduced form thereof according to the present invention is described with reference to the drawings.

In the first example described below, human blood plasma is employed as a specimen containing coenzyme Q-10 and a 2-electron reduced form thereof. Also, in the second example, human saliva is employed as a specimen containing coenzyme Q-10 and a 2-electron reduced form thereof.

Figure 4:
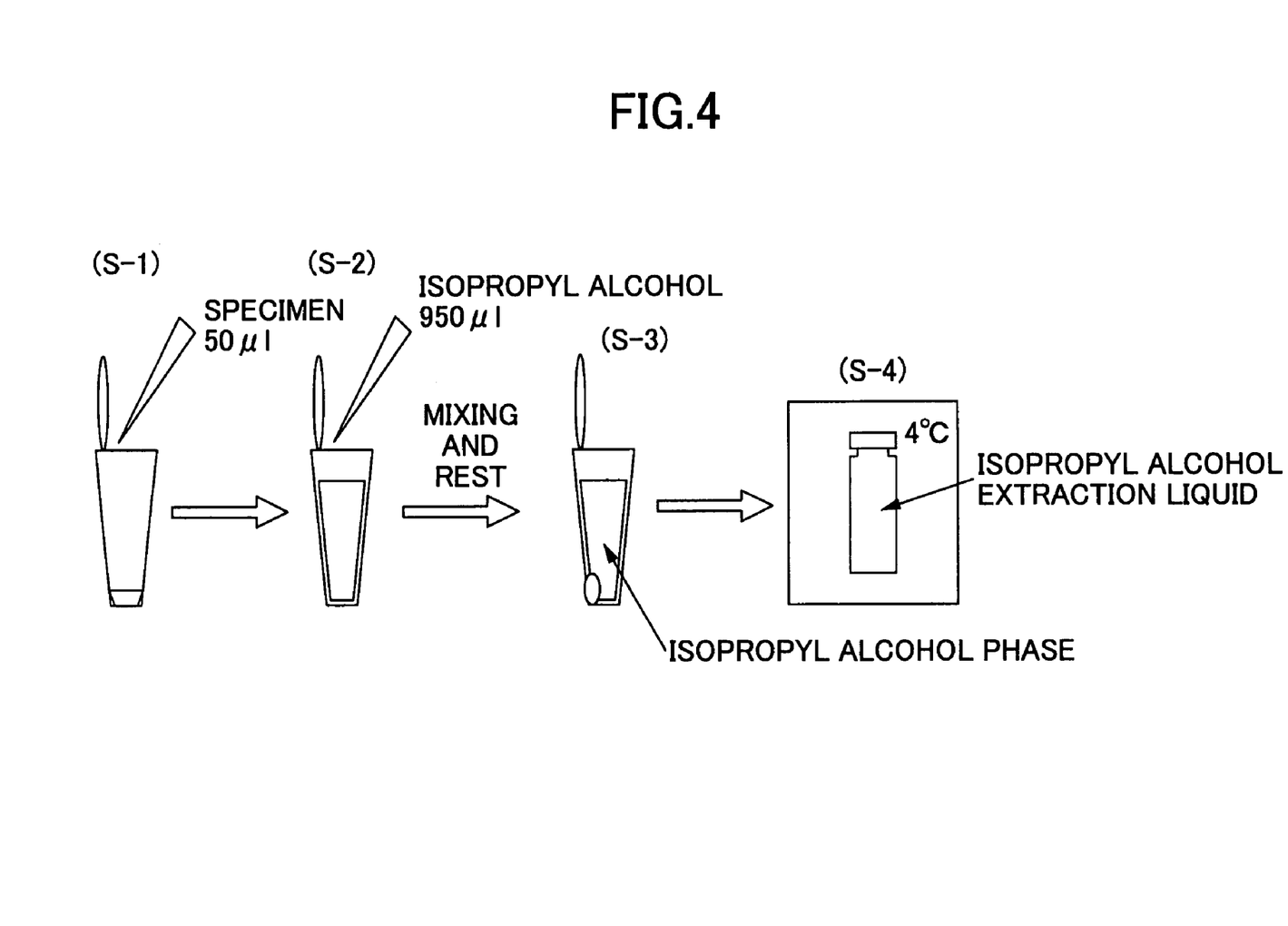
FIG. 4 is a diagram for illustrating a pretreatment process in an analysis method for coenzyme Q-10 and a 2-electron reduced form thereof.

First, a pretreatment in the analysis method for coenzyme Q-10 and a 2-electron reduced form thereof according to the first example is described with reference to FIG. 4.

50 µl of human blood plasma as a specimen is sampled (S-1 in FIG. 4), 950 µl of isopropyl alcohol is added into it (S-2 in FIG. 4), and then they are mixed sufficiently. Subsequently, they are subjected to a centrifugal separator at a rotational speed of 12,000 rpm for 3 minutes and at a temperature of 4° C. Thus, coenzyme Q-10 and a 2-electron reduced form thereof are extracted from the specimen into an isopropyl alcohol phase (S-3 in FIG. 4).

Figure 5A:
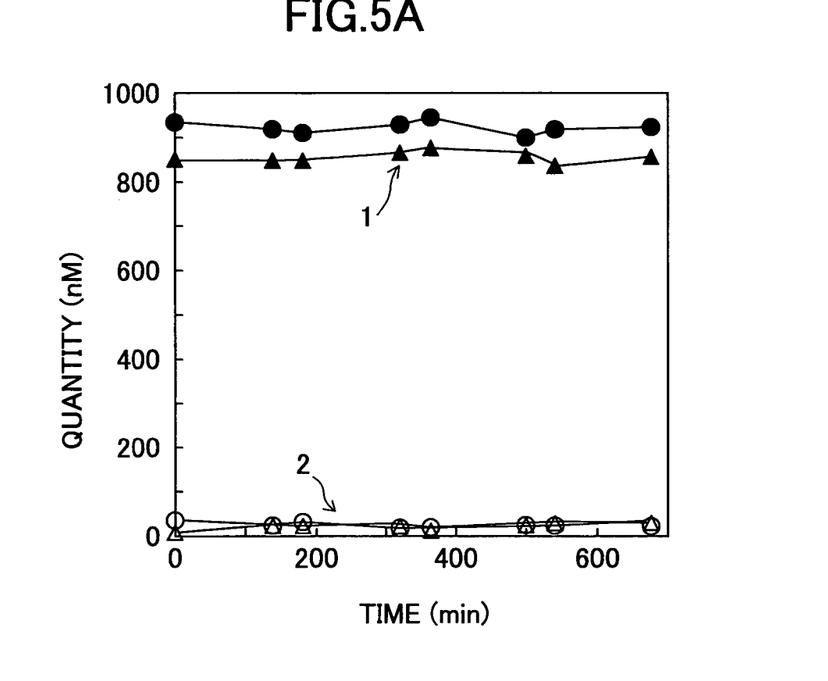
FIG. 5A is a graph diagram showing variation in a component with time when an extracted liquid is stored after a pretreatment in an analysis method according to the present example, with respect to the quantities of coenzyme Q-10 and a 2-electron reduced form thereof.
Figure 5B:
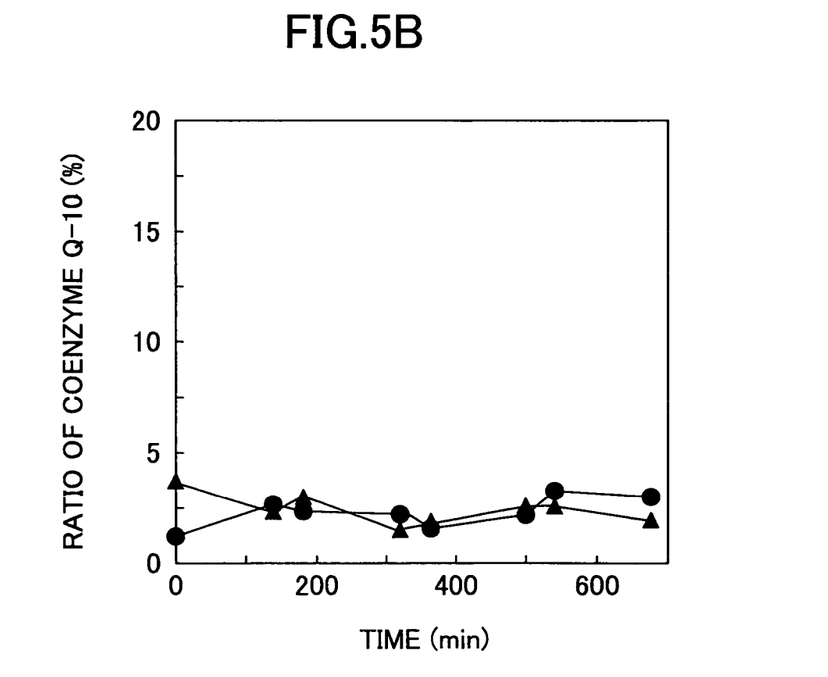
FIG. 5B is a graph diagram showing variation in a component with time when an extracted liquid is stored after a pretreatment in an analysis method according to the present example, with respect to the molar fraction of coenzyme Q-10.

When an extracted liquid into which the coenzyme Q-10, etc., has been extracted is stored at a temperature around 4° C. (S-4 in FIG. 4), the 2-electron reduced form of coenzyme Q-10 is rarely oxidized even after at least 11 hours, as shown in FIG. 5. Thus, the alteration of a stored analytical sample can be prevented. Additionally, the longitudinal axis in regard to coenzyme Q-10 in FIG. 5(*b*) represents the ratio (molar-ratio) of the coenzyme Q-10 occupied in the total quantity of the coenzyme Q-10 and the 2-electron reduced form thereof.

Due to the pretreatment method of the first example according to the present embodiment as described above, an analytical sample obtained by extracting coenzyme Q-10 and a 2-electron reduced form thereof from a specimen can be stored at a stable state for a long period of time. Then, as the extracted liquid is an analytical sample, an accurate analysis can be provided. Accordingly, for example, a large amount of specimen can be continuously and automatically processed by setting the extracted liquid as an analytical sample to an auto-sampler of which the temperature is controlled at 4° C.

Herein, the temperature of 4° C. is a usual operating temperature when a biological sample is the specimen, and the alteration of other components can be prevented by keeping the biological sample at this temperature. If the biological sample is at a temperature significantly over this temperature, the alteration of a component such as the 2-electron reduced form of coenzyme Q-10 cannot be avoided. On the other hand, if the biological sample is frozen and stored, a step of defrosting the biological sample is required for analysis and the continuous and automatic process using the above-mentioned auto-sampler, etc., cannot be easily realized.

Therefore, the temperature of around 4° C. in the present invention is intended to include both a temperature higher than 4° C. and a temperature lower than 4° C., as long as the biological sample as described above can be maintained without alteration. That is, the storage temperature of the extracted liquid may be within a range of the melting point of a water-soluble organic solvent for extraction through ordinary temperature. In the first example, since isopropyl alcohol is employed as the water-soluble organic solvent for extraction, the lower limit of the storage temperature results in −89.5° C. that is the melting point of isopropyl alcohol.

Next, a method for analyzing an extracted liquid stored for a required time as an analytical sample by HPLC is described below.

Figure 6:
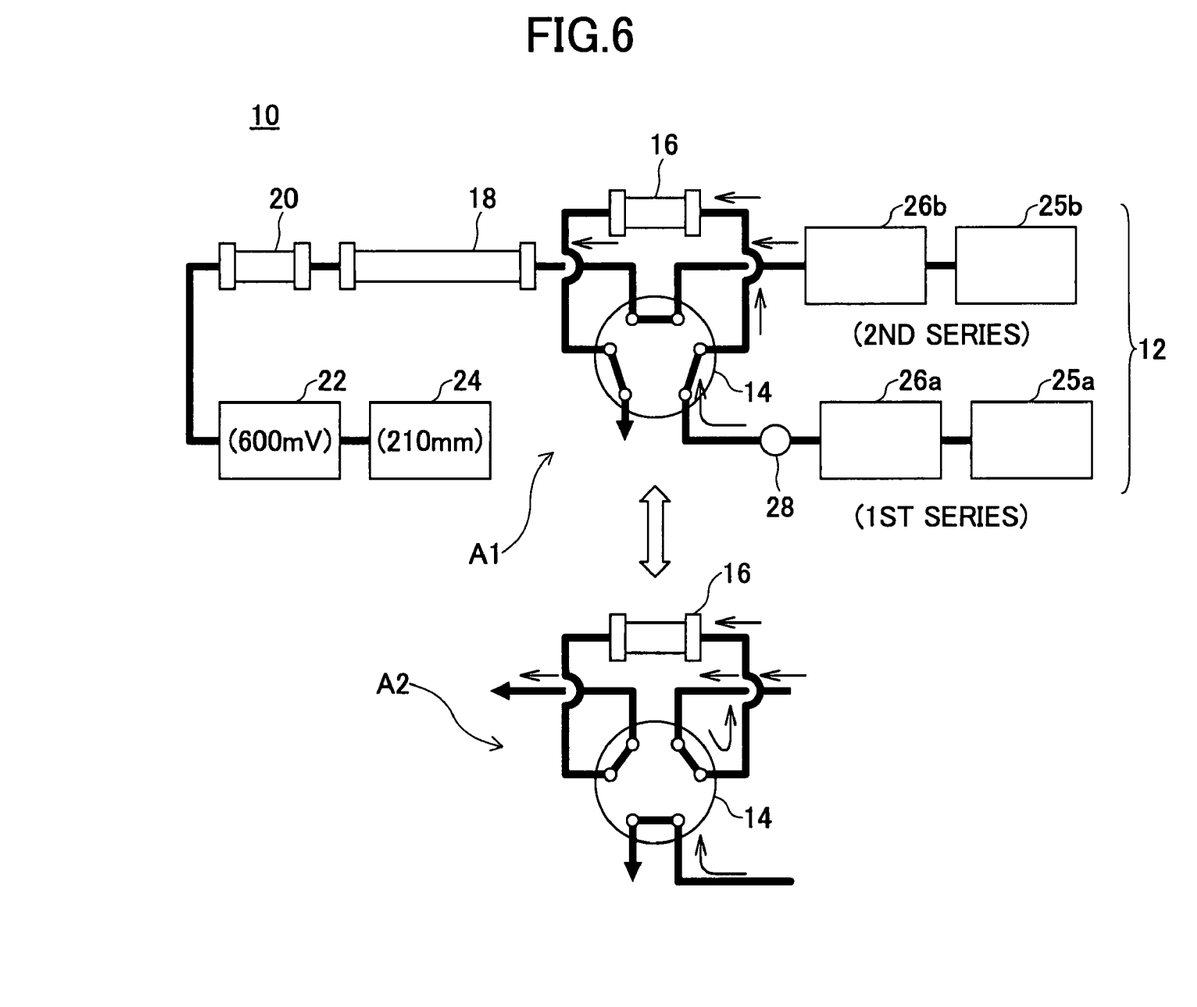
FIG. 6 is a diagram showing a general configuration of an analysis system for coenzyme Q-10 and a 2-electron reduced form thereof.

First, an analysis system used for an analysis method according to the present invention is described with reference to FIG. 6. An analysis system 10 according to the present embodiment includes a liquid-sending mechanism 12, a switching mechanism 14, a concentration column 16, a separation column 18, a reduction column 20, an electrochemical detector 22, and an ultraviolet absorption detector 24.

The liquid-sending mechanism 12 is composed of two series, i.e., the first and second series, and each series includes a storage container 25a, 25b for a mobile phase, and a pump 26a, 26 for liquid-sending the mobile phase of the storage container 25a, 25b. The first series further includes a sample injector 28.

In the storage container 25a of the first series, a mixed solution of methanol and water (an aqueous solution of 95% ethanol), which contains 50 mM of sodium perchlorate, is stored as the mobile phase. On the other hand, in the storage container 25b of the second series, a mixed solution of methanol and isopropyl alcohol (a solution of 90% ethanol), which contains 50 mM of sodium perchlorate, is stored as the mobile phase.

For either of the pumps 26a, 26b, for example, Inert Pump 3001 produced by Shiseido Co., Ltd. can be employed. This Inert Pump 3001 is a constant flow rate and constant pressure type dual piston pump due to a pulse motor, in which the flux rate is 1 through 3,000 µl/min and the upper limit of the discharge pressure is 35 MPa.

The sample injector 28 provided in the first series is for entraining an analytical sample with the mobile phase of the first series, for which an appropriate apparatus can be employed and an auto-sampler is preferably employed.

Where an auto-sampler is employed as the sample injector 28, for example, Autosampler 3023 produced by Shiseido Co., Ltd. can be employed. In regard to the Autosampler 3023, the sample injection quantity is 0.1 through 400 µl (controllable by 0.1 µl), the number of treated samples is 100 through 200, and the temperature can be controlled within a range of 4 through 20° C. by means of electron cooling.

The switching mechanism 14 is for switching liquid-sending routes for the mobile phases of the two series of the liquid-sending mechanism 12. In a mode indicated by an arrow A1 (referred to as mode A1, below) in FIG. 6, the mobile phase of the first series is sent to the concentration column 16 and liquid exiting from the concentration column 16 in which coenzyme Q-10, etc., is eliminated is ejected. On the other hand, the mobile phase of the second series bypasses the column 16 and is directly sent to the separation column 18.

On the contrary, in a mode indicated by an arrow A2 (referred to as mode A2, below), the mobile phase of the first series is ejected out of the system so as to stop the liquid-sending to the concentration column 16, and the mobile phase of the second series is sent to the concentration column 16, whereby liquid entraining a concentrated analytical sample (liquid based on the second mobile phase) is sent from the concentration column 16 to the separation column 18. Thus, the concentrated analytical sample is entrained with the mobile phase of the second series and sent to the separation column 18.

The switching mechanism 14 is composed of, for example, a switching valve and, as such a switching valve, for example, a High-Pressure Six-Way Switching Valve 3011 produced by Shiseido Co., Ltd. can be employed. The High-Pressure Six-Way Switching Valve 3011 is a SUS 6-port 2-position valve and the withstand pressure thereof is 35 MPa. Additionally, the connection relation of pipes and the like used in the analysis system 10, which include pipes and the like used in that switching mechanism 14, is apparent from FIG. 6 and SUS is employed as a material for the pipes in order to prevent the adsorption of the coenzyme Q-10 and the 2-electron reduced form thereof.

The concentration column 16 is for concentrating the analytical sample using, for example, the adsorption effect of filler, etc., and, for example, LC-8 produced by SUPELCO can be employed, as previously described.

The separation column 18 is for separating liquid sent out from the concentration column 16 and, for example, LC-8 produced by SUPELCO can be employed.

The reduction column 20 is for reducing liquid sent out from the separation column and, specifically, a column intended to covert the coenzyme Q-10 in the analytical sample to the 2-electron reduced form thereof. As the reduction column 20, for example, SHISEIDO CQ produced by Shiseido Co., Ltd. can be employed.

The electrochemical detector 22 is intended to analyze the 2-electron reduced form of coenzyme Q-10, which can be detected electrochemically and with high sensitivity, and, for example, Electrochemical Detector 3005 produced by Shiseido Co., Ltd. can be employed. The Electrochemical Detector 3005 is a three-pole potentiostatic type and an applied voltage can be set digitally by 10 mV within a range of ±1990 mV.

The ultraviolet absorption detector 24 is for analyzing a component with a high absorption'sensitivity to ultraviolet rays such as cholesterol contained in blood plasma being the analytical sample according to need. As the ultraviolet absorption detector 22, for example, an UV-VIS Detector 3002 produced by Shiseido Co., Ltd. can be employed. The UV-VIS Detector 3002 is a double-beam single-cell type and the wavelength range is 195 through 700 nm.

40 μl of the above-mentioned extracted liquid after the pretreatment is prepared as the analytical sample. 2.0 μl of human blood plasma is contained in the 40 μl analytical sample.

First, the switching mechanism 14 is set to the mode A2 and the mobile phase of the second series (a solution of 90% methanol) stored in the storage container 25b is flown through respective columns of the concentration column 16, the separation column 18, and the reduction column 20 using the pump 26b, so that the respective columns are stabilized. Then, liquid-sending to the separation column 18 and the reduction column 20 may be made at mode A1 according to need.

Basically, this column stabilizing operation has only to be performed once and, subsequently, even if plural analytical samples are analyzed sequentially, it is not necessary to repeat the above-mentioned stabilizing operation each time. However, in the column switching method, the mobile phase of the second series may be sent to each column before and after switching of the switching mechanism 14, for the purpose of performing an analysis at a more stable state.

Subsequently, the mobile phase of the first series (an aqueous solution of 95% methanol) stored in the storage container 25a is liquid-sent to the concentration column 16 using the pump 26a, which entrains the above-mentioned analytical sample using the sample injector 28 in mid-flow. Then, the flow rate is 400 μl/min and the discharge pressure of the pump is 1 MPa. In the concentration column 16, main components such as coenzyme Q-10 and a 2-electron reduced form thereof in the analytical sample are retained. The residual liquid is ejected out of the system.

Subsequently, the mobile phase of the second series (the solution of 90% methanol) stored in the storage container 25b is liquid-sent to the concentration column 16 in which the above-mentioned main components are retained, using the pump 26b. Then, the flow rate is 800 μl/min and the discharge pressure of the pump is 10.1 MPa.

Additionally, these operations are performed using the switching mechanism 14 as described above.

Herein, when an auto-sampler is employed as the sample injector 28 so as to process the analytical sample kept at a temperature of 4° C. continuously and automatically, it is more preferable to liquid-send the mobile phase of the second series to a column beyond the separation column 18 constantly through the switching mechanism 14 while the concentrated analytical sample is not sent. Then, the flow rate is 800 μl/min and the discharge pressure of the pump is 7.6 MPa.

Thus, the liquid entraining the analytical sample in which the main components are concentrated is liquid-sent to the separation column 18 and the reduction column 20 in series, the separation of the main components (as object components for analysis) based on the coenzyme Q-10 and the 2-electron reduced form thereof in the analytical sample is performed, and further a component to be reduced based on the coenzyme Q-10 is reduced.

The liquid treated in the reduction column 20 is sent to the electrochemical detector 22 and the ultraviolet absorption detector 24 in series and detection-processed.

Figure 7:
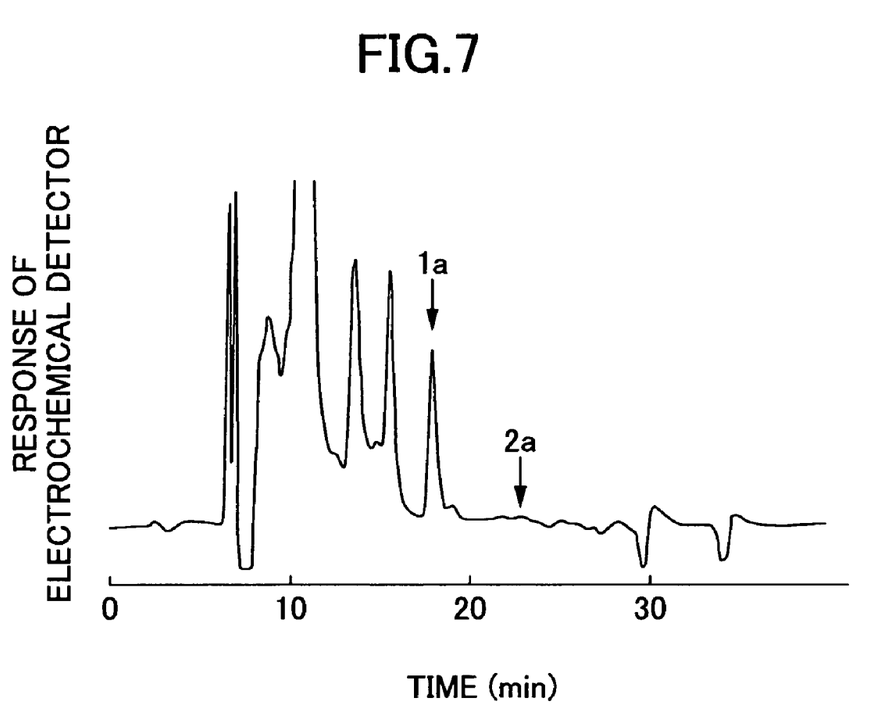
FIG. 7 is one example of a chromatogram obtained by the analysis system in FIG. 6, when blood plasma is employed as a specimen.

One example of a chromatogram using human blood plasma as a specimen, which is obtained by the electrochemical detector 22, is shown in FIG. 7. The set applied voltage of the electrochemical detector 22 is 600 mV. In FIG. 7, arrow 1a denotes a peak of the 2-electron reduced form of coenzyme Q-10 (ubiquinol) and arrow 2a denotes a peak of the coenzyme Q-10 (ubiquinone).

Next, the pretreatment in the analysis method for coenzyme Q-10 and a 2-electron reduced form thereof according to the second example is described. Since only the specimen is different from that of the above-mentioned first example (the human blood plasma in the first example), the description is provided using FIG. 4 similar to the description for the first example.

40 μl of human saliva as a specimen is sampled (S-1 in FIG. 4), a 950 μl of isopropyl alcohol is added into it (S-2 in FIG. 4), and then they are mixed sufficiently. Subsequently, they are subjected to a centrifugal separator at a rotational speed of 12,000 rpm for 3 minutes and at a temperature of 4° C. Thus, coenzyme Q-10 and a 2-electron reduced form thereof are extracted from the specimen to an isopropyl alcohol phase (S-3 in FIG. 4).

Then, an extracted liquid in which the coenzyme Q-10, etc., has been extracted is stored at a temperature around 4° C. (S-4 in FIG. 4). Similar to the first example, the alteration of an analytical sample during storage can also be prevented in the second example. Therefore, the analytical sample in which coenzyme Q-10 and a 2-electron reduced form thereof have been extracted can be also stored at a stable state for a long period of time in the second example. Then, the extracted liquid is the analytical sample used to perform an accurate analysis. Additionally, since other conditions are identical to those of the first example as previously described, the description of them is omitted.

Next, a method for analyzing the extracted liquid subjected to the above-mentioned pretreatment and stored for a required time as an analytical sample using a HPLC is described below.

An analysis method in the second example of the present embodiment is basically identical to the analysis method in the first example described above. Therefore, the analysis method in the second example is simply described. Additionally, since those described previously with reference to FIG. 6 are used as a HPLC and analysis system used for analysis without change, the description for the HPLC and analysis system is omitted.

40 μl of the extracted liquid after the above-mentioned pretreatment is prepared as an analytical sample. The 40 μl of the analytical sample contains 2.0 μl human saliva.

First, the switching mechanism 14 is set to the mode A2 and the mobile phase of the second series (a solution of 90% methanol) stored in the storage container 25b is flown through respective columns of the concentration column 16, the separation column 18, and the reduction column 20 using the pump 26b, so that the respective columns are stabilized. Herein, Capcel Pack C18 AQ S5 (commercial name) with a diameter of 2.0 mm×a length of 35 mm can be employed as the concentration column 16. Also, Capcel Pack C18 AQ S5 (commercial name) with a diameter of 2.0 mm×a length of 250 mm can be employed as the separation column 18. Further, SHISEIDO CQ (commercial name) with a diameter of 2.0 mm×a length of 20 mm can be employed as the reduction column 20.

Subsequently, the mobile phase of the first series (an aqueous solution of 95% methanol) stored in the storage container 25a is liquid-sent to the concentration column 16 using the pump 26a, which entrains the above-mentioned analytical sample using the sample injector 28 in mid-flow. Then, the flow rate is, for example, 200 μl/min. In the concentration column 16, main components such as coenzyme Q-10 and a 2-electron reduced form thereof in the analytical sample are retained. The residual liquid is ejected out of the system.

Subsequently, the mobile phase of the second series (the solution of 90% methanol) stored in the storage container 25b is liquid-sent to the concentration column 16 in which the above-mentioned main components are retained, using the pump 26b.

Herein, an auto-sampler is employed as the sample injector 28 and the analytical sample kept at a temperature of 4° C. is continuously provided to the separation column 18. Thus, the liquid entraining the analytical sample in which the main components are concentrated is liquid-sent to the separation column 18 and the reduction column 20 in series, the separation of the main components (as object components for analysis) based on the coenzyme Q-10 and the 2-electron reduced form thereof in the analytical sample is performed, and further a component to be reduced based on the coenzyme Q-10 is reduced. Then, the flow rate is, for example, 400 μl/min. The liquid treated in the reduction column 20 is sent to the electrochemical detector 22 and the ultraviolet absorption detector 24 in series and detection-processed.

Figure 8:
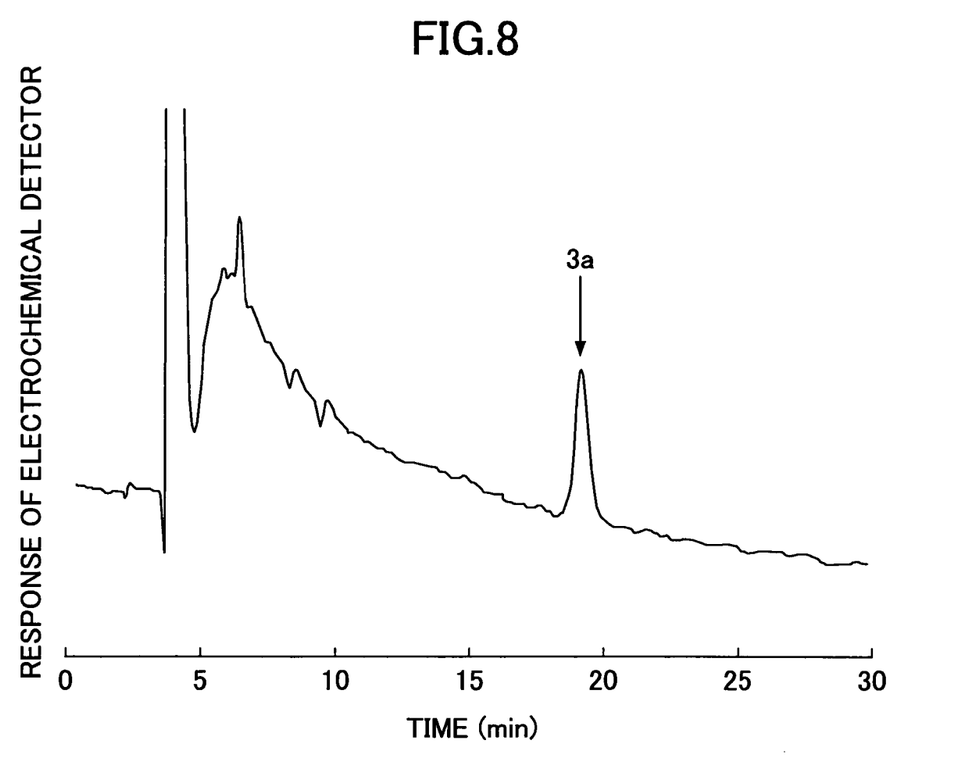
FIG. 8 is one example of a chromatogram obtained by the analysis system in FIG. 6, when saliva is employed as a specimen.

One example of a chromatogram using human saliva as a specimen, which is obtained by the electrochemical detector 22, is shown in FIG. 8. In FIG. 8, arrow 3a denotes a peak of the coenzyme Q-10.

According to the analytical method and analytical system for coenzyme Q-10 and a 2-electron reduced form thereof in the first and second examples as described above, since extracted liquid in which coenzyme Q-10 and 2-electron reduced form thereof have been extracted from a specimen is an analytical sample and a concentrated analytical sample is analyzed, an accurate and highly sensitive analysis can be performed.

Also, according to the analytical method and analytical system for coenzyme Q-10 and a 2-electron reduced form thereof in the first and second examples, coenzyme Q-10 and a 2-electron reduced form thereof are analyzed simultaneously and, preferably, since a large number of specimens are treated continuously and automatically, an efficient analysis can be performed.

Further, in the analytical method and analytical system for coenzyme Q-10 and a 2-electron reduced form thereof in the second example, saliva is employed as a specimen. Since the sampling of saliva is noninvasive in contrast to the sampling of blood (plasma), it is possible to perform self-sampling and the amounts of coenzyme Q-10 and a 2-electron reduced form thereof inside the body can be easily detected.

As described above, according to an analytical method for coenzyme Q-10 and a 2-electron reduced form thereof of the present invention, since a specimen containing at least one of coenzyme Q-10 and a 2-electron reduced form thereof is extracted with a water-soluble organic solvent as a pretreatment and the extracted liquid is analyzed as an analytical sample, an accurate analysis can be performed. Also, it is not necessary to perform an analysis immediately after sampling the specimen.

Also, according to an analytical method for coenzyme Q-10 and a 2-electron reduced form thereof of the present invention, since preparatory treatment for concentrating an analytical sample by a column switching method is performed, even if the concentrations of coenzyme Q-10 and 2-electron reduced form thereof in the analytical sample are low, an analysis can be performed accurately and with high sensitivity.

Also, according to an analytical method for coenzyme Q-10 and a 2-electron reduced form thereof of the present invention, since extracted liquid from a specimen containing both coenzyme Q-10 and a 2-electron reduced form thereof is an analytical sample, and the coenzyme Q-10 and the 2-electron reduced form thereof are separated, further subjected to a reduction treatment, and subsequently detected by a detector, an efficient analysis can be performed.

Also, according to an analytical system for coenzyme Q-10 and a 2-electron reduced form thereof of the present invention, since a liquid-sending mechanism that includes the first series for liquid-sending an analytical sample with the first mobile phase and the second series for liquid-sending only the second mobile phase, a switching mechanism for switching liquid-sending routes for the mobile phases of the two series of the liquid-sending mechanisms, a condensation column for receiving the second mobile phase after the mobile phase of the first series is received so as to condense the analytical sample, a separation column for receiving and separating liquid sent from the condensation column, a reduction column for receiving and reducing liquid sent from the separation column, and an electrochemical detector for detection-processing liquid sent from the reduction column are included, an analysis method of the present invention can be preferably realized.

The invention claimed is:

1. A method of quantifying coenzyme Q-10 and a 2-electron reduced form thereof contained in a specimen, comprising the steps of:
    extracting said coenzyme Q-10 and 2-electron reduced form thereof from said specimen using a water-soluble organic solvent selected from the group consisting of isopropyl alcohol and a solvent having a polarity comparable to that of isopropyl alcohol, so as to obtain an extraction liquid which contains extracted coenzyme Q-10 and 2-electron reduced form thereof;
    concentrating said extracted coenzyme Q-10 and 2-electron reduced form thereof using a concentration column and a first mobile phase, so as to obtain concentrated coenzyme Q-10 and 2-electron reduced form thereof;
    separating said concentrated coenzyme Q-10 and 2-electron reduced form thereof using a separation column and a second mobile phase which is different from said first mobile phase, so as to obtain separated coenzyme Q-10 and 2-electron reduced form thereof;
    reducing said separated coenzyme Q-10 using a non-coulometric cell reduction column; and
    detecting said reduced coenzyme Q-10 and said separated 2-electron reduced form using a detector.

2. The method of quantifying coenzyme Q-10 and a 2-electron reduced form thereof contained in a specimen, as claimed in claim 1, further comprising the step of storing said extraction liquid at a temperature within a range of room temperature to a melting point of said extraction liquid.

3. An analysis system of analyzing coenzyme Q-10 and a 2-electron reduced form thereof contained in an analytical sample, comprising
    a first liquid-feeding mechanism for feeding a first mobile phase with said analytical sample;
    a second liquid-feeding mechanism for feeding a second mobile phase;
    a switching mechanism for switching between said first liquid-feeding mechanism and said second liquid-feeding mechanism;

a condensation column for concentrating said coenzyme Q-10 and 2-electron reduced form thereof, when said first mobile phase with said analytical sample is fed;

a separation column for separating said coenzyme Q-10 and said 2-electron reduced form thereof that are concentrated on said condensation column, when said second mobile phase is fed;

a non-coulometric cell reduction column for reducing said coenzyme Q-10 so as to obtain a reduced coenzyme Q-10; and an electrochemical detector for detecting said reduced coenzyme Q-10 and said 2-electron reduced form thereof.

4. The analysis system of analyzing coenzyme Q-10 and a 2-electron reduced form thereof contained in an analytical sample as claimed in claim 3, which further comprises an ultraviolet absorption detector.

* * * * *